US00PP31621P2

(12) United States Plant Patent
Lintott et al.

(10) Patent No.: US PP31,621 P2
(45) Date of Patent: Mar. 31, 2020

(54) ***LEUCANTHEMUM* PLANT NAMED 'REAL SNOWBALL'**

(50) Latin Name: ***Leucanthemum* x *superbum***
Varietal Denomination: Real Snowball

(71) Applicants: Jennifer Muriel Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 0 days.

(21) Appl. No.: 16/501,940

(22) Filed: Jul. 8, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ..... A01H 5/02; A01H 6/14
See application file for complete search history.

*Primary Examiner* — Annette H Para
(74) *Attorney, Agent, or Firm* — Barbara Campbell; Cochran Freund & Young LLC

(57) ABSTRACT

A new cultivar of *Leucanthemum* plant named 'Real Snowball' that is distinguishable by tight clumping basal branching and upright plant habit, domed to hemispherical inflorescences consisting of numerous whorls of pure white, tubular ray florets. Flowering of 'Real Snowball' commences in late June and continues until October on plants which are 40 cm in height and 35 cm in width after 1 year of growth from an initial cutting.

2 Drawing Sheets

Genus and species: *Leucanthemum* x *superbum*.
Variety denomination: 'Real Snowball'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Snowball'. This application is co-pending with the application for the inventors' variety of *Leucanthemum* plant named 'Real Deal' U.S. patent application Ser. No. 16/501,889.

*Leucanthemum* is a genus within the family Asteraceae in which the commonly referred to "flower" is botanically the inflorescence which is comprised of outer showy ray florets surrounding smaller disc florets.

'Real Snowball' arose and was selected from an ongoing breeding program which was conducted in a nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Snowball' is a seedling selection that resulted from the controlled pollination in 2011 of a single plant of the inventors' proprietary *Leucanthemum* seedling code 'L9050-10' (unreleased and unpatented) as the female parent, using pollen from a single plant of the inventors' proprietary *Leucanthemum* seedling code 'L9023-8' (unreleased and unpatented) as the male parent. The inventors selected 'Real Snowball' in 2013 for its combination of tight clumping basal branching and upright habit, and domed to hemispherical large inflorescences which are pure white in color and held on strong flower stems.

'Real Snowball' was first asexually propagated by the inventors in West Sussex, United Kingdom in 2014 using the method of vegetative division and subsequently by basal shoot cuttings. Since that time under careful observation 'Real Snowball' has been determined uniform, stable and true to type in subsequent generations of asexual propagation.

SUMMARY

The following traits have been repeatedly observed and represent the distinguishing characteristics of 'Real Snowball'. In combination these traits set 'Real Snowball' apart from all other existing varieties of *Leucanthemum* known to the inventor. 'Real Snowball' has not been tested under all possible conditions and phenotypic differences may be observed with variations in environmental, climatic, and cultural conditions, however, without any variance in genotype.

1. 'Real Snowball' exhibits tight clumping basal-branching and an upright plant habit.
2. A fully expanded inflorescence of 'Real Snowball' is 7 cm to 8 cm in diameter and is comprised of numerous, at least 80, pure white ray florets arranged around a central disc.
3. The ray florets of 'Real Snowball' are tubular or quilled in shape with flared free petal lobes.
4. The ray florets of 'Real Snowball' are arranged in multiple concentric whorls.
5. As the inflorescence of Real Snowball' develops, the ray florets are first arranged as dome and then as a hemisphere which occludes the central disc.

6. Flowering of 'Real Snowball' commences in late June and continues until October.
7. After one year of growth in a 2-gallon container, or planted in the ground, a plant of 'Real Snowball' is 40 cm in height and 35 cm in width.
8. 'Real Snowball' is hardy in USDA Zone 5 (−20° F. or −28° C.).

BRIEF DESCRIPTION OF THE PHOTOGRAPHS

The accompanying color photographs illustrate the overall appearance of 'Real Snowball' showing the color of foliage and inflorescence as true as is reasonably possible to obtain in color reproductions of this type. The illustrated plants had been grown in 2-gallon containers outdoors, without any pruning or use of chemical growth regulators. The colors in the photographs may differ from color values cited in the detailed botanical description, which accurately describe the actual color of 'Real Snowball'.

BOTANICAL DESCRIPTION OF THE PLANT

Figure 1:
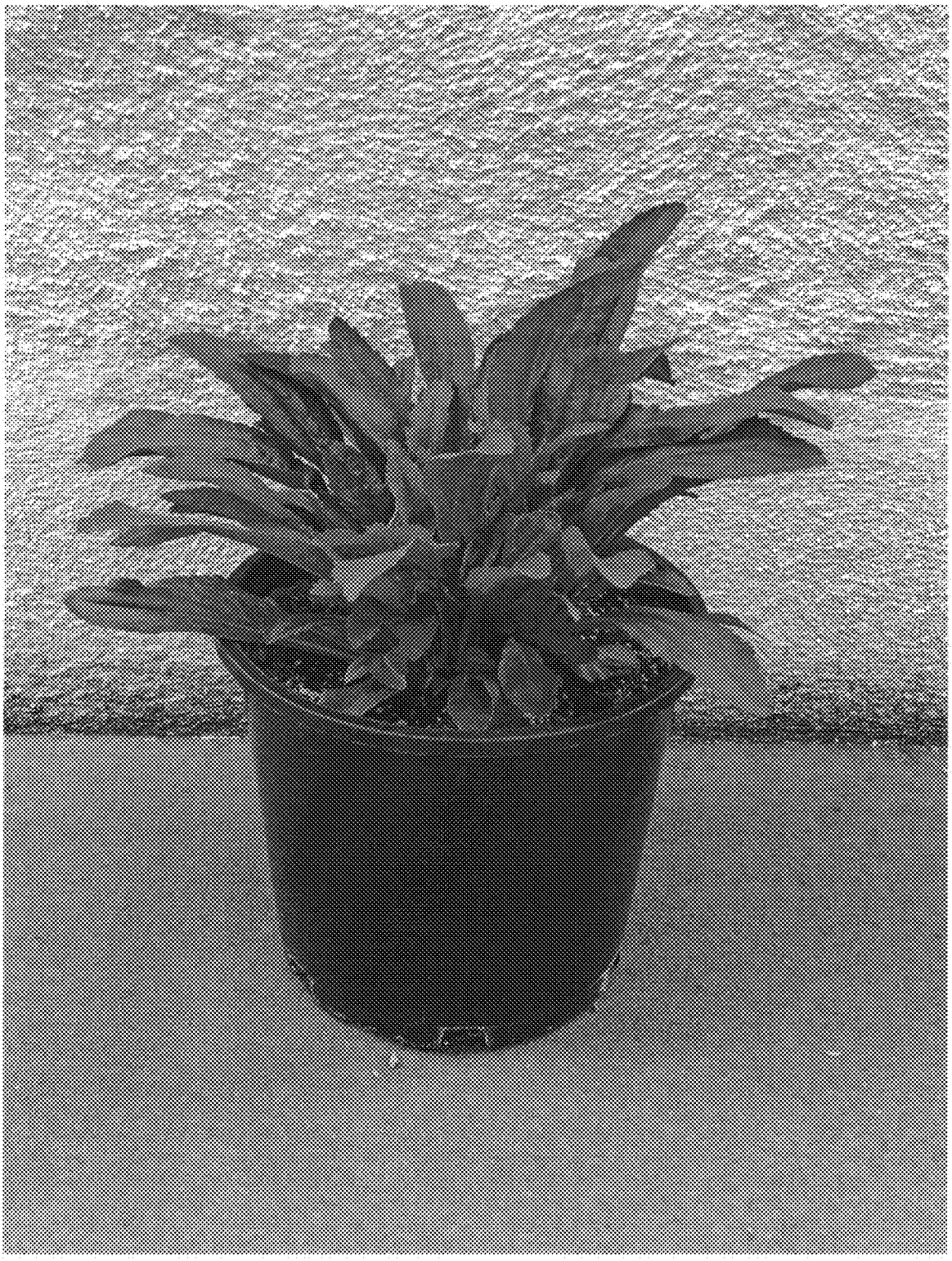
FIG. 1 illustrates the foliage of a four-month-old plant of 'Real Snowball' which has been grown outdoors in a 2-gallon container in Oxnard, Calif.
Figure 2:
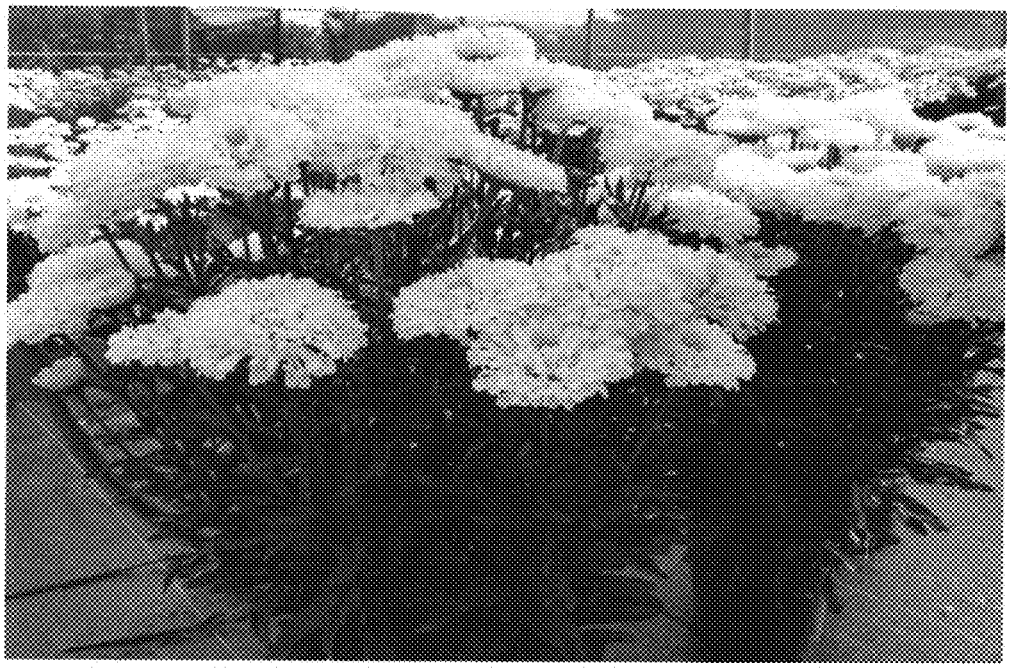
FIG. 2 depicts, in the foreground, two one-year old plants in full flower which have been grown out of doors at the inventors' nursery in West Sussex, United Kingdom.
Figure 3:
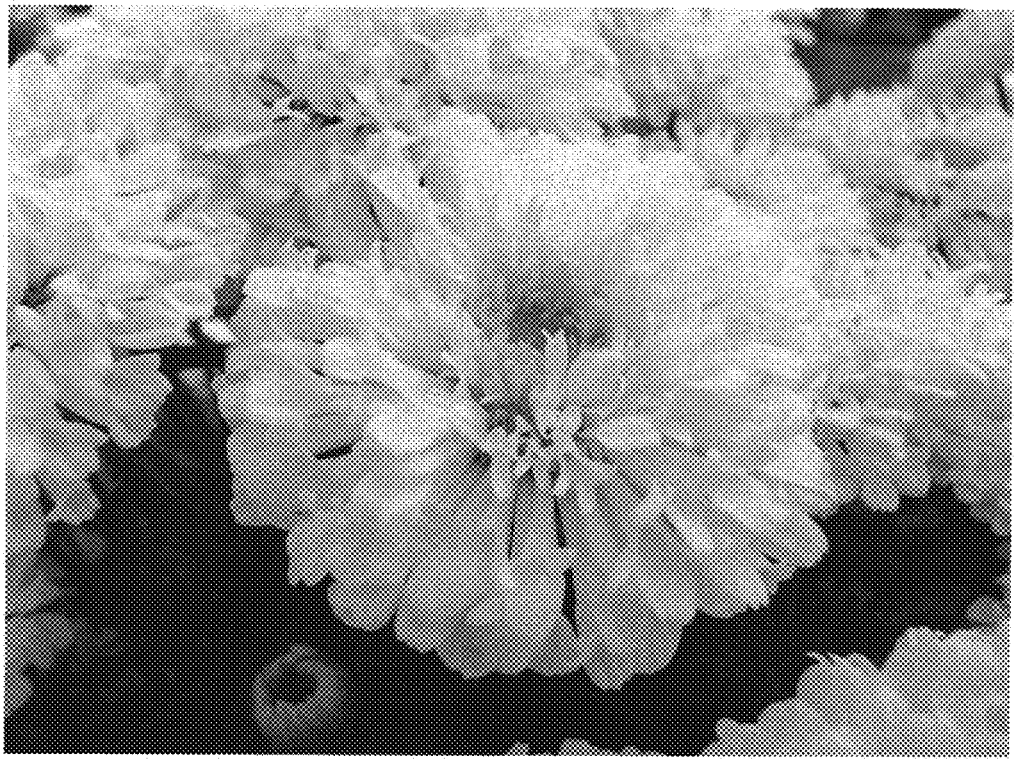
FIG. 3 depicts a close-up view of the inflorescences of 'Real Snowball' using the same plants illustrated in FIG. 2.

The following is a detailed botanical description of the new cultivar 'Real Snowball'. Observations, measurements, values and comparisons were collected in Santa Barbara, Calif. during late June 2019, from a 1-year-old plant growing outdoors in 2-gallon container. Color determinations are made in accordance with The 2007 Royal Horticultural Society Colour Chart from London, England, except where general color terms of ordinary dictionary significance are used.

Botanical classification:

*Family.*—Asteraceae (formerly Compositae).

*Genus.*—*Leucanthemum.*

*Species.*—x *superbum.*

*Denomination.*—'Real Snowball'.

*Common name.*—Shasta daisy.

*Habit.*—Vigorous basal-branching upright growth habit.

*Commercial category.*—Perennial.

*Use.*—For garden and landscape.

*Suggested commercial container size.*—4-inch, 1-gallon, 2-gallon containers.

*Parentage.*—*Leucanthemum* x *superbum* 'Real Snowball' is a seedling selection resulting from the controlled cross-pollination of the following parents: Male parent: inventors' proprietary *Leucanthemum* seedling code 'L9023-8'. Female parent: inventors' proprietary *Leucanthemum* seedling code 'L9050-10'.

*Propagation method.*—Basal shoot cuttings, division and tissue culture.

*Rooting system.*—Fine and fibrous.

*Vigor.*—Vigorous.

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—7 to 8 months to produce a flowering plant in a 1-gallon container starting from a rooted cutting; 10 months to produce a full plant in a 2-gallon container.

*Plant dimensions* (*one year*).—40 cm in height and 35 cm in width.

*Cultural requirements.*—Grow in full sun and rich, moist moderately fertile well-draining soil.

*Pest or disease resistance and susceptibility.*—No specific disease or pest resistance or susceptibility has been observed or is known to the inventor.

*Hardiness.*—USDA Zone 5.

Stem: Underground basal rosette or crown.

Foliage:

*Type* (*division*).—Simple.

*Arrangement.*—Basal rosette.

*Internode.*—Absent: leaves arise from basal rosette or crown.

*Margin.*—Serrate; 12 to 16 teeth spaced at 6 mm to 8 mm intervals, depth 1 mm to 2 mm.

*Margin surface.*—Faintly puberulent; hairs fine, silver-grey in color.

*Apex.*—Acute.

*Base.*—Truncate.

*Leaf attachment.*—Sessile.

*Leaf color.*—Adaxial surface N137D, abaxial surface 137A.

*Leaf shape.*—Lanceolate.

*Leaf dimensions* (*fully developed*).—22 cm in length, 4 cm in width.

*Leaf venation.*—Pinnate; adaxial midrib depressed, abaxial midrib prominently raised, approximately 1 mm in height.

*Vein color* (*both surfaces*).—138B.

*Leaf surface* (*adaxial surface*).—Glabrous, semi-glossy, puberulent in parts only, hairs very short, fine, silver-grey.

*Leaf surface* (*abaxial surface*).—Glabrous, matte.

Inflorescence:

*Inflorescence type.*—Capitulum, consisting of ray florets and disc florets.

*Inflorescence shape.*—Initially expands to form horizontal dome, becoming hemispherical at maturity.

*Inflorescence quantity per plant.*—20 (approximate average).

*Inflorescence diameter* (*when hemispherical and fully opened*).—7 cm to 8 cm.

*Inflorescence depth.*—4.5 cm.

*Inflorescence aspect.*—Upright.

*Inflorescence colors* (*when fully developed*).—Outer (lower) ray florets: Pure white, whiter than NN155D. Inner (nearest to disc) ray florets: 12A to 12B. Central disc: 17A.

*Fragrance.*—Pleasant, characteristic of freshly cut grass.

*Blooming season.*—Late June to October.

*Lastingness of inflorescence* (*range*).—10 to 14 days on the plant; ray florets are persistent.

Bud:

*Bud dimensions* (*prior to opening*).—0.75 cm in height and 1.25 cm in diameter.

*Bud shape.*—Flattened sphere.

*Bud color.*—147B.

*Bud surface.*—Glabrous.

Ray florets:

*Ray floret arrangement.*—Whorled, consisting of five or more concentric whorls of primary outer ray florets and irregularly formed secondary inner ray florets nearest the disc.

*Shape.*—Tubular, quilled, corolla tube subtends large lower petal lobe and typically two smaller upper petal recurving lobes.

*Quantity.*—80 to 120 per inflorescence.

*Aspect.*—Inner ray florets (nearest to disc) upright; outer ray florets horizontal to upward facing as inflorescence becomes hemispherical.

*Dimensions* (*including corolla tube*).—Inner ray florets (nearest to disc): 0.8 cm to 1.5 cm in length and 3 mm to 5 mm in width. Outer ray florets: 2.0 cm to 2.5 cm in length, 5 mm to 9 mm in width.

*Color* (*both surfaces*).—Inner ray florets, 12A to 12B; outer ray florets: pure white, whiter than NN155D.

*Corolla tube dimensions.*—5 mm to 6 mm in length, 2 mm to 3 mm in diameter.

*Corolla tube color.*—NN155D.

Ray floret petals:

*Outer ray florets.*—Petal shape: 5 petals fused longitudinally to form corolla tube then separating into one large tripartite lower petal lobe and two smaller upper petal lobes. Petal lobe aspect: Lower lobe reflexed downwards; upper lobes strongly recurved. Surface (corolla tube and petal lobes): Glabrous. Petal lobe apex: Rounded, lower lobe emarginate. Petal lobe margin: Entire. Petal lobe dimensions: Lower petal lobe: 5 mm in length, 5 mm in width. Upper petal lobes: 3 mm to 4 mm in length, 2 mm to 3 mm in width. Petal lobe color (both surfaces): pure white, whiter than NN155D.

*Inner ray florets.*—Petal shape: Varies between tubular with petal lobes and strap like. Petal dimensions: 0.8 cm to 1.5 cm in length and 3 mm to 5 mm in width. Petal surface: Glabrous. Petal margin: Entire. Petal color (both surfaces): 12A to 12B.

Disc floret:

*Disc diameter.*—2.5 cm to 3.0 cm.

*Disc floret quantity* (*average*).—Approximately 220 to 250 per inflorescence, massed at center of receptacle.

*Disc floret color.*—17A.

*Disc floret dimensions.*—6 mm to 7 mm in length, 1 mm in diameter.

*Disc floret shape.*—Tubular.

*Disc floret petal quantity.*—Ranges from 3 to 5 in number, basally fused.

*Disc floret petal dimensions.*—3 mm in length, 0.75 mm to 1.0 mm in width.

*Disc floret petal color.*—17A.

*Disc floret petal apex.*—Acute.

*Disc floret petal base.*—Truncate.

*Seed.*—Observed and similar shape and type as with other *Leucanthemums*.

COMPARISON WITH PARENTAL LINES AND KNOWN VARIETY

In comparison with its parents, both of which bear white flowers, 'Real Snowball' is smaller and more compact in size and habit, and bears inflorescences which are hemispherical when fully developed and are comprised of numerous whorls of ray flowers. The inflorescences of the female parent 'L9050-10' are smaller and slightly convex. The inflorescences of the male parent 'L9023-8' are disc-shaped and are comprised of only two rows (layers) of ray florets.

The commercial variety of *Leucanthemum* which the inventors consider to most closely resemble 'Real Snowball' is the inventors' variety of *Leucanthemum* Plant Named 'Real Galaxy' (U.S. Plant Pat. No. 23,873). Whereas the inflorescences of both 'Real Snowball' and 'Real Galaxy' are comprised of very numerous tubular ray flowers, the ray flowers of 'Real Snowball' are wide and flared and arranged in many whorls eventually forming a hemisphere, and the ray flowers of 'Real Galaxy' are tubular and narrow and are arranged horizontally.

We claim:

1. A new and distinct cultivar of *Leucanthemum* plant named 'Real Snowball' as described and illustrated herein.

* * * * *